United States Patent [19]

Yeowell et al.

[11] 4,144,263
[45] Mar. 13, 1979

[54] BENZYL CYANOACETALS

[75] Inventors: David A. Yeowell, Chapel Hill; Roy A. Swaringen, Jr., Durham, both of N.C.

[73] Assignee: Burroughs Wellcome Co., Research Triangle Park, N.C.

[21] Appl. No.: 804,537

[22] Filed: Jun. 8, 1977

[30] Foreign Application Priority Data

Jun. 9, 1976 [GB] United Kingdom ............... 23756/76

[51] Int. Cl.² .................. C07C 121/75; C07C 121/76; C07C 121/78; C07D 239/48
[52] U.S. Cl. ........................... 260/465 D; 260/465 E; 260/465 F; 544/323
[58] Field of Search ............ 260/465 F, 465 D, 465 E

[56] References Cited

U.S. PATENT DOCUMENTS

| 2,576,939 | 12/1951 | Hitchings et al. | 260/256.4 N |
|---|---|---|---|
| 2,579,259 | 12/1951 | Hitchings et al. | 260/256.4 N |
| 2,755,298 | 7/1956 | Whittaker | 260/465 |
| 3,341,541 | 9/1967 | Hoffer | 260/256.4 N |
| 3,772,289 | 11/1973 | Roth | 260/256.4 N |

FOREIGN PATENT DOCUMENTS

| 1620729 | 8/1970 | Fed. Rep. of Germany. |
| 2341213 | 8/1976 | Fed. Rep. of Germany. |
| 2341214 | 10/1976 | Fed. Rep. of Germany. |
| 278885 | 8/1974 | France. |
| 10614 | 8/1974 | Netherlands. |

OTHER PUBLICATIONS

De Wolfe, "Carboxylic Ortho Acid Derivatives," Academic Press, N.Y., pp. 234–248 (1970).
Stavely et al., *J. Am. Chem. Soc.*, 73, pp. 3448–3450, (1951).
Russell et al., *J. Am. Chem. Soc.*, 74, pp. 1310–1313, (1952).

*Primary Examiner*—Dolph H. Torrence
*Attorney, Agent, or Firm*—Donald Brown

[57] ABSTRACT

Benzyl cyanoacetals of formula:

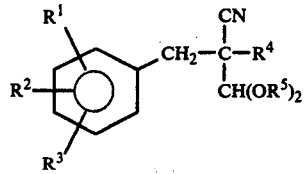

wherein $R^1$, $R^2$ and $R^3$ are the same or different and each is a halogen or a hydrogen atom, an alkoxy group, an alkyl group, or a dialkylamino group; $R^4$ is an alkoxycarbonyl group, or an aldehyde group;

and $R^5$ is an alkyl group; the alkyl or alkoxy groups each having from 1 to 4 carbon atoms, and their use as intermediates in the preparation of antibacterial 2,4-diamino-5-benzylpyrimidines. They are prepared from a reaction between an orthoester and an α-substituted-β-benzylpropionitrile and then the resulting cyanoacetal is converted to the benzylpyrimidine by reaction with guanidine.

14 Claims, No Drawings

BENZYL CYANOACETALS

This invention relates to novel benzyl cyanoacetals, their process of preparation and, in particular, their use as intermediates in the preparation of 2,4-diamino-5-benzylpyrimidines.

It is known that 2,4-diamino-5-benzylpyrimidines possess antibacterial and/or antimalarial activity and that such activity can be potentiated by using the pyrimidine in conjunction with a sulphonamide. One pyrimidine which is most useful is that commonly known as trimethoprim (2,4-diamino-5-(3',4',5'-trimethoxybenzyl)pyrimidine), and such is the degree of potentiation obtained with this compound that its use with a sulphonamide, such as sulphamethoxazole, in the treatment of various infections has met with considerable success.

There are also known many processes which are suitable for the preparation of 2,4-diamino-5-benzylpyrimidines. Most of the important ones (e.g. those disclosed in U.K. Pat. Nos. 957,797, 1,133,766, 1,142,654 and 1,261,455) utilise, as starting materials, an appropriately substituted benzaldehyde and a β-substituted propionitrile. These are reacted together under conditions specified in the respective patent specifications to provide an intermediate substance which can then be cyclised with guanidine to the required 2,4-diamino-5-benzylpyrimidine. Although these processes, and in particular those of U.K. Pat. Nos. 1,133,766 and 1,261,455, enable the production of such pyrimidines in most reasonable yields, they unfortunately possess little flexibility in the manner in which the intermediate substance is obtained. Thus, in the event of a shortage of one of the starting materials, the commercial operation of any of these processes could be jeopardised.

Therefore, it is an object of the present invention to provide a class of intermediates which can cyclise with guanidine to give a 2,4-diamino-5-benzylpyrimidine and which can be prepared from a variety of starting materials. It is a further object to provide an overall process which uses readily available starting materials, requires no unusual apparatus or reaction conditions, and proceeds with high yields to give 2,4-diamino-5-benzylpyrimidines.

The novel class of intermediates provided by the present invention are the benzyl cyanoacetals of formula (I):

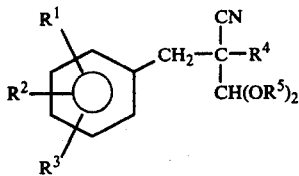

wherein $R^1$, $R^2$ and $R^3$ are the same or different and each is a halogen or hydrogen atom, an alkoxy group, an alkyl group, or a dialkylamino group; $R^4$ is an alkoxycarbonyl group or an aldehyde group; and $R^5$ is an alkyl group; the alkyl or alkoxy groups each having from 1 to 4 carbon atoms.

$R^1$, $R^2$, $R^3$ are preferably methyl or methoxy groups or a hydrogen atom. In particular, $R^1$, $R^2$ and $R^3$ are such that the phenyl ring is substituted in the 3-, 4-, and 5-positions with methoxy groups, or in the 3- and 4-positions with methoxy groups, or in the 2-position with a methyl group and in the 4- and 5-positions with methoxy groups.

Preferred examples for $R^4$ when it is an alkoxycarbonyl group are methoxy and, in particular, ethoxy carbonyl groups. Additionally an alkoxycarbonyl group may be a butoxycarbonyl group.

$R^5$ is conveniently a methyl or ethyl group.

An especially preferred class of benzyl cyanoacetals consists of those where $R^1$, $R^2$ and $R^3$ are 3,4,5-trimethoxy-; $R^4$ is an ethoxycarbonyl or aldehyde group; and $R^5$ is a methyl or ethyl group. These benzyl cyanoacetals are the most preferred intermediates for the synthesis of the important antibacterial trimethoprim.

The present invention also provides a method of preparing the benzyl cyanoacetals of formula (I), as herein defined, which comprises a reaction between a compound of formula (II):

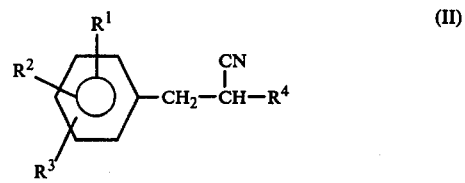

wherein $R^1$, $R^2$, $R^3$ and $R^4$ are as herein defined, and an orthoester of formula (III):

wherein $R^5$ is as herein defined.

In every case to date the orthoester itself is capable of acting as the solvent and therefore no additional solvent is necessary. If, however, it is considered desirable to employ an additional solvent in the reaction, then it should be of a polar aprotic nature and compatible with and capable of dissolving both reactants. Examples of such solvents include dioxan, dimethylformamide, dimethylsulphoxide, and hexamethylphosphoramide.

The reaction is preferably carried out at reflux temperature in an apparatus which enables removal of the alcohol derived from the orthoester. The period of reflux varies according to the reactants used, but generally periods between 1 and 20 hours are considered sufficient to complete the reaction.

In the case where $R^4$ is an alkoxycarbonyl group, the starting material formula (II) can be conveniently obtained in situ from an initial reaction of the correspondingly substituted benzyl cyanoacetic acid and the orthoester of formula (III).

Occasionally, the use of a co-reactant, such as an acid anhydride, in which the alkyl groups have from 1 to 4 carbon atoms, for example acetic anhydride, in the reaction may be advantageous in that its use may allow a more facile reaction, and moreover obviates the necessity to remove the alcohol derived from the orthoester. Indeed, it can be even more advantageous first to combine the orthoester and acid anhydride in order to form an intermediate, and then react the intermediate so formed with the compound of formula (II). Accordingly, the present invention further provides another method of preparing the benzyl cyanoacetals of formula (I), as herein defined, which comprises a reaction between a compound of formula (II), as herein defined, and a compound of formula (IV),

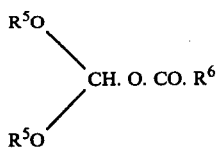
(IV)

wherein $R^6$ is an alkyl group having from 1 to 4 carbon atoms and $R^5$ is as herein defined.

The compound of formula (IV), for example, diethoxymethyl acetate, may in turn be prepared by the reaction between an orthoester of formula (III), as herein defined, and an acid anhydride in which the alkyl groups have from 1 to 4 carbon atoms. Thus, in the preparation of diethoxymethyl acetate, triethyl orthoformate and acetic anhydride are reacted together.

Again when the benzyl cyanoacetals of formula (I) are prepared from compounds of formula (IV) which in turn are prepared either separately or in situ from the reaction between an orthoester of formula (III) and an acid anhydride, there is no need to remove during the reaction the alcohol derived from the orthoester.

The orthoesters of formula (III) and the compounds of formula (II) can be obtained commercially or be prepared by methods described in the literature. For example, compounds of formula (II) may be prepared by a method which comprises condensing a benzaldehyde of formula (V):

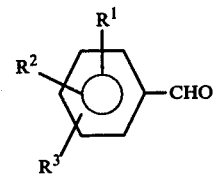
(V)

wherein $R^1$, $R^2$ and $R^3$ are as herein defined, with a compound of formula (VI):

$$R^4 - CH_2CN \qquad (VI)$$

wherein $R^4$ is as herein defined, and catalytically or chemically hydrogenating the resulting compound of formula (VII):

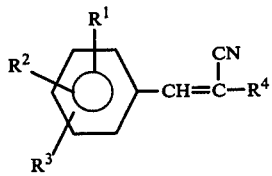
(VII)

wherein $R^1$, $R^2$, $R^3$ and $R^4$ are as herein defined.

Compounds of formula (II) can also be prepared by the reaction between a compound of formula (VIII):

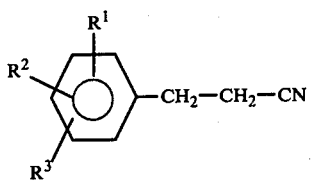
(VIII)

and a compound of formula (IX):

$$R^4\text{-Q} \qquad (IX)$$

wherein $R^1$, $R^2$, $R^3$ and $R^4$ are as herein defined and wherein Q is a leaving group, especially an alkoxide.

A third method of preparation of a compound of formula (II) comprises the mono-benzylation with a compound of formula (X):

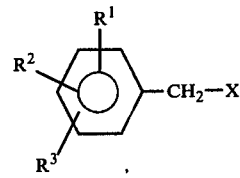
(X)

wherein $R^1$, $R^2$ and $R^3$ are as herein defined and X is a leaving group, especially a halogen atom, of a compound of formula (VI), as herein defined. In practice a large excess of the compound of formula (VI) may be required to suppress di-benzylation.

It can be seen from the above that the benzyl cyanoacetals of formula (I) can be prepared from a wide variety of starting materials, many of which are well-known and commercially available at comparatively low prices. Thus, if there is a shortage of one of the starting materials, the benzyl cyanoacetal intermediate of formula (I) can still be prepared by an alternative synthesis of comparable economic benefit, an option which is not available to such an extent with the known processes.

The benzyl cyanoacetals of formula (I) are useful intermediates in the synthesis of 2,4-diamino-5-benzylpyrimidines. It should be noted however that some of the benzyl cyanoacetals may be somewhat unstable and should therefore be stored at low temperature, or more preferably, immediately converted to the desired end-product.

The present invention further provides a method for preparing a 2,4-diamino-5-benzylpyrimidine of formula (XI):

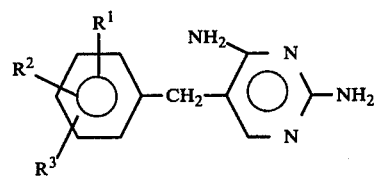
(XI)

wherein $R^1$, $R^2$ and $R^3$ are as herein defined, which comprises reacting a benzyl cyanoacetal of formula (I), as herein defined, with guanidine in a solvent compatible with and capable of dissolving both reactants.

Solvents which may be employed in this reaction are preferably alcohols having from 1 to 4 carbon atoms, for example ethanol, and the reaction itself is desirably carried out at reflux temperature for a period of time from about 1 hour to 30 hours.

When $R^4$ in the benzyl cyanoacetal of formula (I) is an alkoxycarbonyl group, it may be desirable to perform the reaction in the presence of additional base, such as potassium hydroxide.

Further advantages of the present invention will now become apparent from the following description of embodiments of the invention, which embodiments do not limit the scope of the invention in any way.

EXAMPLE 1

Preparation of α-Dimethoxymethyl-α-formyl-β-(3,4,5-trimethoxyphenyl)propionitrile A solution of α-formyl-β-(3,4,5-trimethoxyphenyl) propionitrile (17.2 g, 0.069 mol) in trimethyl orthoformate (100 ml) was heated at reflux for 3 hours using a steam jacketed column for continuous removal of methanol. The solution was cooled and most of the excess orthoformate was removed in vacuo. The residual oil was taken up in ether (100 ml) and crystallisation began almost immediately. The mixture was filtered to yield light tan crystals (9.4 g, 42%, m.p. 117°–121° C.). Recrystallisation from cyclohexane-chloroform gave colourless needles of α-dimethoxymethyl-α-formyl-β-(3,4,5-trimethoxyphenyl)propionitrile, m.p. 118°–122° C.; ir bands at 2250cm$^{-1}$ (C≡N) and 1738cm$^{-1}$ (CHO); nmr (CDCl$_3$) δ 3.15 (s, 2, Ar-CH$_2$-C), 3.57 and 3.62 (singlets, 6, CH(OCH$_3$), 3.87 (s, 9, -C$_6$H$_2$(OCH$_3$)$_3$), 4.50 (s, 1, CH(OCH$_3$)$_2$), 6.53 (s, 2, aromatic H), and 9.53 (s, 1, CHO). Anal. Calcd for C$_{16}$H$_{21}$NO$_6$: C, 59.43; H, 6.55; N, 4.33. Found: 59.44; H, 6.60; N, 4.33.

EXAMPLE 2

Preparation of α-Diethoxymethyl-α-formyl-β-(3,4,5-trimethoxyphenyl)propionitrile Using the same procedure as Example 1 but with triethyl orthoformate in place of trimethyl orthoformate, there was obtained α-diethoxymethyl-α-formyl-β-(3,4,5-trimethoxyphenyl)propionitrile (78%, m.p. 109°–115° C.). Recrystallisation from ether-acetone gave the analytical sample (m.p. 117°–121° C.). Anal. Calcd for C$_{16}$H$_{21}$NO$_6$: C, 61.52; H, 7.17; N. 3.99. Found: C, 61.31; H, 7.21; N, 3.87.

EXAMPLE 3

Preparation of 2,4-Diamino-5-(3,4,5-trimethoxy benzyl)pyrimidine

α-Diethoxymethyl-α-formyl-β-(3,4,5-trimethoxyphenyl) propionitrile (35.1 g, 0.10 mol) was added to an ethanolic solution of guanidine (from 0.35 mol of guanidine hydrochloride). The mixture was heated at reflux for a total of 6.5 hours during which time enough ethanol was allowed to boil off to bring the reaction temperature up to 85°. The dark solution was allowed to cool and stand overnight. The mixture was filtered, and the solid was washed with cold ethanol and dried to yield crude product (24.4 g, 84.1%). Purification was effected by dissolving the crude product in hot aqueous acetic acid and reprecipitation with concentrated ammonium hydroxide. The precipitate was washed twice with water, once with cold acetone, and dried to yield 2,4-diamino-5-(3,4,5-trimethoxybenzyl)pyrimidine (19.5 g, 67.2%), m.p. 197°–198° C. (identity confirmed by nmr). The acetone was concentrated in vacuo to dryness yielding additional though somewhat less pure trimethoprim (2,5 g, 8.6%, m.p. 194°–196° C.).

EXAMPLE 4

Preparation of α-Carbethoxy-α-diethoxymethyl-β-(3,4,5-trimethoxyphenyl)propionitrile A solution of ethyl 3,4,5-trimethoxybenzylcyanoacetate (14.7g) in triethyl orthoformate (100 ml) was heated at reflux for 18 hours using a steam-jacketed column for continuous removal of ethanol. The solution was cooled, and most of the excess orthoformate was removed in vacuo. The crystals obtained were washed with ether and dried to yield colourless crystals of α-carbethoxy-α-diethoxymethyl-β-(3,4,5-trimethoxy phenyl)propionitrile (16.3 g, 82%), m.p. 91°; nmr (CDCl$_3$) δ1.13, 1.20. and 1.32 (triplets, 9, CH$_3$CH$_2$O-), 3.15 (s, 2, Ar-CH$_2$-C), 3.4–4.0 (m, 4, m, 4, CH$_3$CH$_2$-O), 3.85 (s, 9, -C$_6$H$_2$-(OCH$_3$)$_3$), 4.13 (q, 2, CH$_3$CH$_2$-OCO), 4.80 (s, 1, -CH (OEt)$_2$), and 6.55 (s, 2, aromatic H). Anal. Calcd. for C$_{20}$H$_{29}$NO$_7$: C, 60.74; H, 7.39; N, 3.54. Found: C, 60.56; H, 7.33; N, 3.64.

EXAMPLE 5

Preparation of 2,4-diamino-5-(3,4,5-trimethoxybenzyl)pyrimidine

A solution of α-carbethoxy-α-diethoxymethyl-β-(3,4,5-trimethoxyphenyl)propionitrile (7.9 g, 0.02 mol) and an equivalent amount of potassium hydroxide in ethanol (50 ml) was heated at reflux for one hour. A solution of guanidine (0.07 mol) in ethanol (50 ml) was added, and reflux was resumed. Some ethanol was allowed to boil off bringing the reaction temperature up to 85°. After about 20 hours at reflux the mixture was allowed to cool, and the product was filtered and washed with ethanol. The crude product was purified by treating with hot aqueous acetic acid and reprecipitation with ammonium hydroxide. The yield of purified trimethoprim (m.p. 197°–198°) was 3.6g (62%), its identity being confirmed by an NMR spectrum.

EXAMPLE 6

Preparation of Ethyl 3,4,5-Trimethoxybenzyl cyanoacetate

Sodium metal (17.7 g, 0.77 g-atom) was added with good agitation to 1040 g (9.2 moles) of ethyl cyanoacetate over a three hour period. The temperature was maintained at 22°–26° with a water bath. The resulting milky white suspension was stirred for an additional hour, cooled to 10°, and 3,4,5-trimethoxybenzyl chloride (83.2 g, 0.384 mole) was added portionwise in two hours. The reaction mixture was then allowed to stir at ambient temperature for 18 hours. The reaction mixture was cooled to 19°–20°, and 960 ml of 5% aqueous acetic acid (v/v) was added. Benzene (1200 ml) was added, and after thorough mixing the layers were separated. The aqueous layer was extracted with 2 × 540 ml. of benzene. The benzene extracts were combined, washed with 1000 ml of water, and dried over magnesium sulfate. The benzene was removed using a rotary evaporator and a 50° water bath. The residue was then vacuum distilled at a pressure of 0.2 mm Hg and a 105°–110° oil bath to remove excess ethyl cyanoacetate. The yield of crude ethyl 3,4,5-trimethoxybenzylcyanoacetate was 107.2 g (95.5%).

EXAMPLE 7

Preparation of Ethyl 3,4,5-Trimethoxybenzyl cyanoacetate

Trimethoxybenzaldehyde was condensed with ethyl cyanoacetate and the resulting product (94.6%) catalytically hydrogenated in accordance with the procedure of U.K. Patent 1 406 307 to give ethyl 3,4,5-trimethoxybenzyl cyanoacetate (91.5%).

EXAMPLE 8

Preparation of Diethoxymethyl acetate

Acetic anhydride (550 g), formic acid (275 g) and triethyl orthoformate (740 g) were reacted as is described in DeWolfe, Synthesis, 1974, 153–172 (scaled up five fold). The product had a b.p. of 77°–78° C. at 25 mm/Hg, and was obtained in a yield of 54.5%.

EXAMPLE 9

Preparation of α-Carbethoxy-α-diethoxymethyl-β-[3,4,5-trimethoxyphenyl]propionitrile Ethyl 3,4,5-trimethoxybenzylcyanoacetate (5 g) was mixed with diethoxymethyl acetate (15 g) and heated at 95° C. overnight. The mixture was cooled and crystallized by addition of ether-hexane (1:1, 25 ml). The product was filtered and dried under reduced pressure giving 4.9 g (73%) of white solid, m.p. 95°–97° C.

EXAMPLE 10

Preparation of α-Carbethoxy-α-diethoxymethyl-β-[3,4,5-trimethoxyphenyl]propionitrile 3,4,5-trimethoxybenzylcyanoacetic acid monohydrate (5 g) was mixed with triethylorthoformate (42 ml) and heated at reflux for 21 hrs. The solvent was removed under reduced pressure and the resultant oil crystallized from ether-hexane giving a white solid (4.4 g) (63%), m.p. 95°–96.5° C.

EXAMPLE 11

Preparation of Ethyl 2-cyano-4',5'-dimethoxy-2'-methylcinnamate

A mixture of 4,5-dimethoxy-2-methylbenzaldehyde (36 g), ethyl cyanoacetate (22.6 g), piperidine (2 g), and acetic acid (0.7 g) in 125 ml benzene was fitted for azeotropic removal of water and heated at reflux for 5 hrs. The mixture was cooled, chloroform (400 ml) added and the resultant solution extracted with 2 × 200 ml water, 200 ml 0.5N hydrochloric acid, 200 ml saturated sodium bicarbonate, 200 ml of water and dried (MgSO$_4$). The volatiles were removed under reduced pressure leaving a yellow solid which was washed with cold methanol and dried under reduced pressure giving 51.5 g (94%) of the title compound. m.p. 142°–144° C.

EXAMPLE 12

Preparation of α-Carbethoxy-β-[4,5-dimethoxy-2-methylphenyl]-propionitrile

A mixture of ethyl 2-cyano-4',5'-dimethoxy-2'-methyl cinnamate (30 g) and 5% palladium on carbon (2 g) in 150 ml ethanol was shaken under a 50 psi atmosphere of hydrogen gas until slightly more (15%) than one equivalent of hydrogen gas was taken up. The catalyst was filtered off and the volatiles removed under reduced pressure leaving a clear yellow oil which solidified on standing at −5° C.; m.p. 39°–40° C., yield 27.6 g (90%).

EXAMPLE 13

Preparation of α-Carbethoxy-α-diethoxymethyl-β-[2-methyl-4,5-dimethoxy-2-methyl phenyl]-propionitrile α-Carbethoxy-β-[2-methyl-4,5-dimethoxyphenyl]-propionitrile (14.7 g) in triethylorthoformate (100 ml) was heated at reflux under a steam cooled condenser for 68 hrs. The triethylorthoformate was removed under reduced pressure and 100 ml of 1:1 ether-hexane was added. After cooling to −5° C., the resultant crystals were filtered off, washed with 1:1 ether-hexane (100 ml) and dried under reduced pressure to give 16.3 g (84%) of tan solid, m.p. 84°–86° C.

EXAMPLE 14

Preparation of 2,4-diamino-5-(4,5-dimethoxy-2-methylbenzyl) pyrimidine (ormetoprim)

A solution of α-carbethoxy-α-diethoxymethyl-β-(4,5-dimethoxy-2-methylphenyl)propionitrile (3.9 g, 0.01 mol) and an equivalent amount of potassium hydroxide in ethanol (70 ml) was heated at reflux for one hour. A solution of guanidine (0.035 mol) in ethanol (50 ml) was added, and reflux was resumed. Ethanol was boiled off until the reaction temperature reached 85° C. After 20 hours at reflux the mixture was allowed to cool, and the product was filtered and washed with ethanol giving 2.57 g (94%) of nearly white solid. After purification as described in Example 5, the product was dried under reduced pressure giving a white solid, m.p. 231°–233° C.

EXAMPLE 15

Preparation of Ethyl 2-cyano-3',4'-dimethoxycinnamate

A mixture of 3,4-dimethoxybenzaldehyde (49.8 g), ethyl cyanoacetate (33.9 g), piperidine (3 g) and acetic acid (1.1 g) in 175 ml benzene was fitted for azeotropic removal of water and heated at reflux overnight. The product was isolated in the manner previously described for Example 11 giving 67.4 g (86%) of light yellow solid, m.p. 149–150° C.

EXAMPLE 16

Preparation of α-Carbethoxy-β-[3,4-dimethoxyphenyl]propionitrile

Ethyl 2-cyano-3',4'-dimethoxycinnamate (26.1 g) was mixed with 150 ml ethanol and 5% palladium on carbon (2 g). The mixture was shaken under a hydrogen atmosphere (50 psi) until slightly more (10%) than one equivalent of hydrogen gas was taken up. The catalyst was filtered off and the volatiles were removed under reduced pressure giving 24.5 g (93%) of a yellow oil. Structure was confirmed by NMR spectroscopy.

EXAMPLE 17

Preparation of α-Carbethoxy-α-diethoxymethyl-β-[3,4-dimethoxyphenyl]propionitrile A mixture of α-Carbethoxy-β-[3,4-dimethoxyphenyl]propionitrile (10 g) and diethoxymethyl acetate (30 g) was heated at 95° C. for 20 hours. The volatiles were removed under vacuum pump pressure leaving 13.4 g (94%) of a nearly colorless oil which solidified on standing at −5° C. to a white solid, m.p. 62°–65° C.

EXAMPLE 18

Preparation of 2,4-diamino-5-(3,4-dimethoxybenzyl)pyrimidine (Diaveridine)

A solution of α-carbethoxy-α-diethoxymethyl-β-(3,4-dimethoxyphenyl)-propionitrile (3.75 g) and an equivalent amount of potassium hydroxide in ethanol (70 ml)

was heated at reflux for one hour. A solution of guanidine (0.035 mol) in ethanol (50 ml) was added and reflux was resumed. Ethanol was boiled off until the reaction temperature reached 85° C. After 17 hours at reflux the mixture was allowed to cool and the product was filtered and washed with ethanol giving a white solid which was purified as described in Example 5 to yield 1.4 g (54%) of the title compound, m.p. 231°–233° C.

What we claim is:

1. A benzyl cyanoacetal of formula (I),

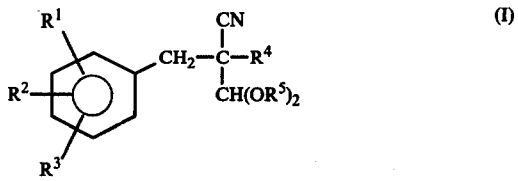

wherein $R^1$, $R^2$ and $R^3$ are the same or different and each is a halogen or hydrogen atom, an alkoxy group, an alkyl group or a dialkylamino group; $R^4$ is an alkoxy carbonyl group or an aldehyde group; and $R^5$ is an alkyl group; the alkyl or alkoxy groups each having from 1 to 4 carbon atoms.

2. A benzyl cyanoacetal according to claim 1, wherein $R^1$, $R^2$ and $R^3$ are the same or different and each is a methyl or methoxy group or a hydrogen atom.

3. A benzyl cyanoacetal according to claim 2, wherein $R^1$, $R^2$ and $R^3$ are methoxy groups substituted in the 3-,4- and 5-positions of the phenyl ring.

4. A benzyl cyanoacetal according to claim 2, wherein $R^1$, and $R^2$ are methoxy groups substituted in the 3- and 4-positions of the phenyl ring and $R^3$ is a hydrogen atom.

5. A benzyl cyanoacetal according to claim 2, wherein $R^1$ is a methyl group substituted in the 2-position of the phenyl ring and $R^2$ and $R^3$ are methoxy groups substituted in the 4- and 5-positions of the phenyl ring.

6. A benzyl cyanoacetal according to claim 1, wherein $R^4$ is an aldehyde group.

7. A benzyl cyanoacetal according to claim 1, wherein $R^4$ is an alkoxycarbonyl group.

8. A benzyl cyanoacetal according to claim 7, wherein the alkoxycarbonyl group is a methoxycarbonyl group.

9. A benzyl cyanoacetal according to claim 7, wherein the alkoxycarbonyl group is an ethoxycarbonyl group.

10. A benzyl cyanoacetal according to claim 7, wherein the alkoxycarbonyl group is a butoxycarbonyl group.

11. A benzyl cyanoacetal according to claim 1, wherein $R^5$ is a methyl or ethyl group.

12. α-Dimethoxymethyl-α-formyl-β-(3,4,5-trimethoxyphenyl) propionitrile.

13. α-Diethoxymethyl-α-formyl-β-(3,4,5-trimethoxyphenyl) propionitrile.

14. α-Carbothoxy-α-diethoxymethyl-β-(3,4,5-trimethoxyphenyl) propionitrile.